United States Patent
De Sausmarez Lintell et al.

(10) Patent No.: US 9,592,342 B2
(45) Date of Patent: Mar. 14, 2017

(54) DELIVERY OF TWO OR MORE MEDICAMENTS THROUGH A SINGLE DOSE SELECTION AND DISPENSE INTERFACE

(75) Inventors: Daniel Thomas De Sausmarez Lintell, Warwickshire (GB); Malcolm Stanley Boyd, Warwickshire (GB); David Martin Leak, Lake Hopatcong, NJ (US); Carmen Patricia Keating, New South Wales (AU); David Sanders, Warwickshire (GB); Elizabeth Anne Marshall, Leamington Spa (GB); Jay Graham, Cheshire (GB); Ross Douglas Laurie MacArthur, Cheshire (GB); Michael James Heald, Cheshire (GB); Christopher James Smith, Cheshire (GB); Elliot Lucas Ortiz, San Francisco, CA (US)

(73) Assignee: Sanofi-Aventis Deutschland GmbH, Frankfurt am Main (DE)

( * ) Notice: Subject to any disclaimer, the term of this patent is extended or adjusted under 35 U.S.C. 154(b) by 735 days.

(21) Appl. No.: 13/375,525

(22) PCT Filed: Jun. 1, 2010

(86) PCT No.: PCT/EP2010/057571
§ 371 (c)(1),
(2), (4) Date: Feb. 21, 2012

(87) PCT Pub. No.: WO2010/139666
PCT Pub. Date: Dec. 9, 2010

(65) Prior Publication Data
US 2012/0136334 A1    May 31, 2012

Related U.S. Application Data

(60) Provisional application No. 61/183,452, filed on Jun. 2, 2009.

(30) Foreign Application Priority Data

Jul. 25, 2009  (EP) ..................... 09009657

(51) Int. Cl.
*A61M 5/31* (2006.01)
*A61M 5/24* (2006.01)
(Continued)

(52) U.S. Cl.
CPC ........ *A61M 5/2448* (2013.01); *A61M 5/3294* (2013.01); *A61M 5/2455* (2013.01);
(Continued)

(58) Field of Classification Search
CPC .............. A61M 5/2448; A61M 5/2455; A61M 5/31551; A61M 5/3294; A61M 2005/3142;
(Continued)

(56) References Cited

U.S. PATENT DOCUMENTS 3,563,240 A  *  2/1971  Silver .......................... 604/87
3,911,916 A  *  10/1975  Stevens ............. A61M 5/31596
604/191

(Continued)

FOREIGN PATENT DOCUMENTS

CN      1507360 A    6/2004
EP      0695555 A1   2/1996
(Continued)

OTHER PUBLICATIONS

First Office Action issued by the Chinese Patent Office for Chinese Patent Application No. 201080033637.0 dated Feb. 7, 2013.
(Continued)

*Primary Examiner* — Laura Bouchelle
*Assistant Examiner* — Justin L Zamory
(74) *Attorney, Agent, or Firm* — McDonnell Boehnen Hulbert & Berghoff LLP

(57) ABSTRACT

An injection system for co-delivery of two medicaments (1, 2) having a drug delivery device (7) containing a primary
(Continued)

reservoir (11) containing a first medicament (1) and having a secondary reservoir (5, 17, 30) containing a second medicament (2) where the drug delivery device (7) has only one dose setter (12) for the primary reservoir (11) and that automatically determines the dose of the second medicament (2). Both medicaments (1, 2) are delivered through a single dispense interface (3, 16, 21, 31).

15 Claims, 4 Drawing Sheets

(51) Int. Cl.
*A61M 5/32* (2006.01)
*A61M 5/315* (2006.01)
*A61M 5/178* (2006.01)

(52) U.S. Cl.
CPC ..... *A61M 5/31551* (2013.01); *A61M 5/31561* (2013.01); *A61M 2005/1787* (2013.01); *A61M 2005/3142* (2013.01)

(58) Field of Classification Search
CPC .. A61M 5/284; A61M 5/2066; A61M 5/1408; A61M 5/31545; A61M 37/0069; A61M 2005/1787; A61J 7/0053
USPC ............. 604/86, 87, 203, 88, 191, 59, 60
See application file for complete search history.

(56) References Cited

U.S. PATENT DOCUMENTS

| | | | |
|---|---|---|---|
| 4,055,177 A * | 10/1977 | Cohen | 604/88 |
| 4,067,333 A | 1/1978 | Reinhardt et al. | |
| 4,755,169 A * | 7/1988 | Sarnoff et al. | 604/511 |
| 4,857,056 A | 8/1989 | Talonn | |
| 5,114,411 A * | 5/1992 | Haber et al. | 604/203 |
| 5,281,198 A * | 1/1994 | Haber et al. | 604/86 |
| 5,681,279 A * | 10/1997 | Roper | A61J 7/0053 604/57 |
| 6,562,002 B1 * | 5/2003 | Taylor | A61M 5/282 604/82 |
| 2002/0007142 A1 | 1/2002 | Hjertman et al. | |
| 2002/0016563 A1 * | 2/2002 | Hill | A61M 5/2066 604/85 |
| 2008/0114304 A1 | 5/2008 | Nalesso et al. | |

FOREIGN PATENT DOCUMENTS

| | | |
|---|---|---|
| JP | 5898932 | 7/1983 |
| JP | 2008535636 | 9/2008 |
| WO | 9412227 A1 | 6/1994 |
| WO | 0189613 A1 | 11/2001 |
| WO | 03000317 A1 | 1/2003 |
| WO | 2005000384 A1 | 1/2005 |
| WO | 2007027203 A2 | 3/2007 |
| WO | 2008107378 A1 | 9/2008 |
| WO | 2008154092 A1 | 12/2008 |

OTHER PUBLICATIONS

English Translation of the First Office Action issued by the Chinese Patent Office for Chinese Patent Application No. 201080033637.0 dated Feb. 7, 2013.

* cited by examiner

DELIVERY OF TWO OR MORE MEDICAMENTS THROUGH A SINGLE DOSE SELECTION AND DISPENSE INTERFACE

FIELD OF THE PRESENT PATENT APPLICATION

This disclosure relates to medical devices and methods of delivering at least two drug agents from separate reservoirs using devices having only a single dispense interface. A single delivery procedure initiated by the user causes a non-user settable dose of a second drug agent and a variable set dose of a first drug agent to be delivered to the patient. The drug agents may be available in two or more reservoirs, containers or packages, each containing independent (single drug compound) or pre-mixed (co-formulated multiple drug compounds) drug agents. Our invention may be of particular benefit where the therapeutic response can be optimized for a specific target patient group, through control and definition of the therapeutic profile.

BACKGROUND

Certain disease states require treatment using one or more different medicaments. Some drug compounds need to be delivered in a specific relationship with each other in order to deliver the optimum therapeutic dose. Here, combination therapy may be desirable, but not possible in a single formulation for reasons such as, but not limited to, stability, compromised therapeutic performance and toxicology.

For example, in some cases it might be beneficial to treat a diabetic with a long acting insulin and with a glucagon-like peptide-1 (GLP-1), which is derived from the transcription product of the proglucagon gene. GLP-1 is found in the body and is secreted by the intestinal L cell as a gut hormone. GLP-1 possesses several physiological properties that make it (and its analogs) a subject of intensive investigation as a potential treatment of diabetes mellitus.

There are a number of potential problems when delivering two active medicaments or "agents" simultaneously. The two active agents may interact with each other during the long-term, shelf life storage of the formulation. Therefore, it is advantageous to store the active components separately and only combine them at the point of delivery, e.g. injection, needle-less injection, pumps, or inhalation. However, the process for combining the two agents needs to be simple and convenient for the user to perform reliably, repeatedly and safely.

A further problem is that the quantities and/or proportions of each active agent making up the combination therapy may need to be varied for each user or at different stages of their therapy. For example, one or more actives may require a titration period to gradually introduce a patient to a "maintenance" dose. A further example would be if one active requires a non-adjustable fixed dose while the other is varied in response to a patient's symptoms or physical condition. This problem means that pre-mixed formulations of multiple active agents may not be suitable as these pre-mixed formulations would have a fixed ratio of the active components, which could not be varied by the healthcare professional or user.

Additional problems arise where a multi-drug compound therapy is required, because many users cannot cope with having to use more that one drug delivery system or make the necessary accurate calculation of the required dose combination. This is especially true for users with dexterity or computational difficulties.

Accordingly, there exists a strong need to provide devices and methods for the delivery of two or more medicaments in a single injection or delivery step that is simple for the user to perform. In specific embodiments, our invention overcomes the above-mentioned problems by providing separate storage containers for two or more active drug agents that are then only combined and/or delivered to the patient during a single delivery procedure. Setting a dose of one medicament automatically fixes or determines the dose of the second medicament (i.e. non-user settable). Moreover, the opportunity may be given for varying the quantity of one or both medicaments. For example, one fluid quantity can be varied by changing the properties of the injection device (e.g. dialing a user variable dose or changing the device's "fixed" dose). The second fluid quantity can be changed by manufacturing a variety of secondary drug containing packages with each variant containing a different volume and/or concentration of the second active agent. The user or healthcare professional would then select the most appropriate secondary package or series or combination of series of different packages for a particular treatment regime.

These and other advantages will become evident from the following more detailed description of the invention.

Problem to be Solved

The problem to be solved by the present invention is to provide a drug delivery system and a method where an administration of at least two medicaments is facilitated.

SUMMARY

In specific embodiments, our invention allows complex combination of multiple drug compounds within a single device. In particular, a user may be enabled to set and dispense a multi-drug compound device through one single dose setting mechanism and a single dispense interface. This single dose setter may control the mechanism of the device such that a predefined combination of the individual drug compounds or medicaments is delivered when a single dose of one of the medicaments is set and dispensed through the single dispense interface. Furthermore the device could be primed with one medicament, whereby priming comprises the output needle and/or the mechanism of the device. Priming could be facilitated by a dedicated flow path or bypass. Although principally described in this application as an injection device, the basic principle could be applicable to other forms of drug delivery, such as, but not limited to, inhalation, nasal, ophthalmic, oral, topical, and like devices.

By defining the therapeutic relationship between the individual drug compounds, our delivery device may help ensure that a patient/user receives the optimum therapeutic combination dose from a multi-drug compound device without the inherent risks associated with multiple inputs, where the user has to calculate and set the correct dose combination every time they use the device. The terms medicament and drug compound are used synonymously within the context of the present invention. The combination of the individual medicaments comprises preferably at least two different drug agents, wherein each medicament comprises at least one drug agent. The medicaments can be fluids, defined herein as liquids or gases or powders that are capable of flowing and that change shape at a steady rate when acted upon by a force tending to change its shape. Alternatively, one of the medicaments may be a solid that is carried, solubilized or otherwise dispensed with another fluid medicament.

The disclosed drug delivery system may be of particular benefit to users with dexterity or computational difficulties as the single input and associated predefined therapeutic profile may remove the need for them to calculate their prescribed dose every time they use the device and the single input allows considerably easier setting and dispensing of the combined compounds.

In a preferred embodiment a master drug compound, such as insulin, contained within a multiple dose, user selectable device could be used with a single use, user replaceable, module that contains a single dose of a secondary medicament and the single dispense interface. When connected to the primary device the secondary compound is activated/delivered on dispense of the primary compound. Although our invention specifically mentions insulin, insulin analogs or insulin derivatives, and GLP-1 or GLP-1 analogs as two possible drug combinations, other drugs or drug combinations, such as an analgesics, hormones, beta agonists or corticosteroids, or a combination of any of the above-mentioned drugs could be used with our invention.

For the purposes of our invention the term "insulin" shall mean Insulin, insulin analogs, insulin derivatives or mixtures thereof, including human insulin or a human insulin analogs or derivatives. Examples of insulin analogs are, without limitation, Gly(A21), Arg(B31), Arg(B32) human insulin; Lys(B3), Glu(B29) human insulin; Lys(B28), Pro (B29) human insulin; Asp(B28) human insulin; human insulin, wherein proline in position B28 is replaced by Asp, Lys, Leu, Val or Ala and wherein in position B29 Lys may be replaced by Pro; Ala(B26) human insulin; Des(B28-B30) human insulin; Des(B27) human insulin or Des(B30) human insulin. Examples of insulin derivatives are, without limitation, B29-N-myristoyl-des(B30) human insulin; B29-N-palmitoyl-des(B30) human insulin; B29-N-myristoyl human insulin; B29-N-palmitoyl human insulin; B28-N-myristoyl LysB28ProB29 human insulin; B28-N-palmitoyl-LysB28ProB29 human insulin; B30-N-myristoyl-ThrB29LysB30 human insulin; B30-N-palmitoyl-ThrB29LysB30 human insulin; B29-N-(N-palmitoyl-Y-glutamyl)-des(B30) human insulin; B29-N-(N-lithocholyl-Y-glutamyl)-des(B30) human insulin; B29-N-(ω-carboxyheptadecanoyl)-des(B30) human insulin and B29-N-(ω-carboxyheptadecanoyl) human insulin.

As used herein the term "GLP-1" shall mean GLP-1, GLP-1 analogs, or mixtures thereof, including without limitation, exenatide (Exendin-4(1-39), a peptide of the sequence H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Pro-Ser-NH$_2$), Exendin-3, Liraglutide, or AVE0010 (H-His-Gly-Glu-Gly-Thr-Phe-Thr-Ser-Asp-Leu-Ser-Lys-Gln-Met-Glu-Glu-Glu-Ala-Val-Arg-Leu-Phe-Ile-Glu-Trp-Leu-Lys-Asn-Gly-Gly-Pro-Ser-Ser-Gly-Ala-Pro-Pro-Ser-Lys-Lys-Lys-Lys-Lys-Lys-NH$_2$).

Examples of beta agonists are, without limitation, salbutamol, levosalbutamol, terbutaline, pirbuterol, procaterol, metaproterenol, fenoterol, bitolterol mesylate, salmeterol, formoterol, bambuterol, clenbuterol, indacaterol.

Hormones are for example hypophysis hormones or hypothalamus hormones or regulatory active peptides and their antagonists, such as Gonadotropine (Follitropin, Lutropin, Choriongonadotropin, Menotropin), Somatropine (Somatropin), Desmopressin, Terlipressin, Gonadorelin, Triptorelin, Leuprorelin, Buserelin, Nafarelin, Goserelin.

One embodiment of our invention relates to a drug delivery system to deliver two or more medicaments through a single dispense interface that comprises a primary reservoir of medicament containing at least one drug agent. A dose button is operably connected to the primary reservoir of medicament. The system has a single dispense interface configured for fluid communication with the primary reservoir and with a secondary reservoir of medicament containing at least one drug agent.

A further embodiment of our invention relates to a drug delivery system to deliver two or more medicaments through a single dose setter and a single dispense interface that comprises a housing containing a single dose setter operably connected to a primary reservoir of medicament containing at least one drug agent. A dose button is also operably connected to the primary reservoir of medicament. Our system has a single dispense interface configured for fluid communication with the primary reservoir and with a secondary reservoir of medicament containing at least one drug agent.

The dose button can be any type of mechanism that triggers the delivery procedure, where driven mechanically or through a combination of electronics and mechanics. The button can move or be a touch sensitive virtual button, for example, a touch sensitive screen. The drug dispense interface can be any type of outlet that allows the two or more medicaments to exit the system and be delivered to the patient. Types of interfaces include hollow needles, catheters, atomizers, pneumatic injectors, or needle-less injectors, mouth-pieces, nasal-applicators and the like interfaces. The delivery mechanism can be of any type utilizing a rotatable piston rod, preferably a rotatable piston rod with two distinct threads.

The containment or reservoir of a secondary medicament within a needle sub-assembly according to our invention is named a medicated module. The secondary reservoir may contain a single dose or multiple doses of medicament. The system is designed such that a single activation of the dose button causes the user settable dose of medicament from the primary reservoir and a non-user set dose of medicament from the second reservoir to be expelled through the single dispense interface. By user settable dose it is meant dose that the user (patient or health care provider) can physically manipulate the device to set a desired dose. Likewise, the user settable dose can be set remotely through the use of wireless communication (Bluetooth, WiFi, satellite, etc.) or the dose could be set by another integrated device, such as a blood glucose monitor after performing a therapeutic treatment algorithm. By non-user set dose it is meant that the user (or any other input) cannot independently set or select a dose of medicament from the secondary reservoir. As an example, when the user (or another input as described above) sets the dose of the primary medicament in the primary reservoir, the dose of the second medicament is automatically set. In an alternative design, the single operation of the dose button causes medicament from the primary reservoir to be expelled through the drug dispense interface after the non-user set dose of medicament has been expelled through the drug dispense interface. In cases where the secondary reservoir contains only a single dose of the second medicament, then this would equal the non-user set dose.

Furthermore, a method of dispensing at least two medicaments from separate reservoirs is disclosed. The method comprises the steps of providing a drug device comprising a primary reservoir of medicament containing at least one drug agent, a dose button operably connected to the primary reservoir of medicament and a single dispense interface configured for fluid communication with the primary reservoir. The drug device may also comprise a housing containing a single dose setter operably connected to the primary reservoir of medicament or any other feature of the disclosed drug device. Furthermore, the method comprises the step of providing a secondary reservoir of medicament containing at least one drug agent configured for fluid communication to the single dispense interface, wherein a single activation of the dose button causes medicament from the primary reservoir and a non-user settable dose of medicament from the secondary reservoir to be expelled through the single dispense interface.

In a further embodiment, a method of dispensing a non-user settable dose of one medicament and a dose of a primary medicament from separate reservoirs comprises the step of setting a dose of a first medicament contained in a primary reservoir using a single dose setter of a drug delivery device. Based on the set dose of the first medicament, a non-user settable dose of a second medicament contained in a secondary reservoir is automatically set. Then, the set dose of the first medicament from the primary reservoir is moved, causing it to flow in a distal direction. The set dose of the first medicament and the non-user settable dose of the second medicament is forced through a single dispense interface.

Moreover, a method of dispensing a fixed dose of one medicament and a variable dose of a second medicament from separate reservoirs is disclosed that involves the steps of first setting a dose of a first medicament contained in a primary reservoir of a drug delivery device having a single dose setter. Next a dose button is activated that moves the set dose of the first medicament from the primary reservoir in a distal direction and simultaneously forcing substantially all of a non-user set dose (e.g. a single dose) of a second medicament from a secondary reservoir through a single dispense interface. Upon completion of the delivery procedure substantially all or a therapeutic dose of the second medicament has been expelled as well as the set dose of the first medicament through the single dispense interface. By "therapeutic dose" or by "substantially all" we mean that at least about 80% of the second medicament is expelled from the drug delivery device, preferably at least about 90% is expelled. In one arrangement, preferably at least about 80% is delivered.

In yet another embodiment, our invention is directed to a drug delivery system, where the containment of a secondary drug compound is within a needle sub-assembly (medicated module) designed for attachment to an associated primary or master delivery device. The actuation of the master device actuates the dispense of the secondary compound and a primary compound contained in a reservoir in the master drug delivery device. The combination of compounds as discrete units or as a mixed unit is delivered to the body via an integral needle. This would provide a combination drug injection system that, from a user's perspective, would be achieved in a manner that very closely matches the currently available injection devices that use standard needles. One possible delivery procedure would involve the following steps:
1. Attach the medicated needle module to the distal end of the primary injection device (e.g. a threaded hub of a cartridge holder containing a 3 ml cartridge of the primary drug compound) such that the proximal end of the medicated needle is in fluidic communication with the primary compound.
2. Dial up/set the primary injection device such that it is ready to dispense the desired dose of the primary compound.
3. Insert the distal end of the medicated needle into the desired injection site. In some designs, insertion of the medicated needle can trigger delivery of the secondary compound.
4. Dose the primary compound by activating a dose button. This may also cause the secondary compound to automatically dispense.
5. Remove and dispose of the medicated needle module.

The medicated module of our invention can be designed for use with any drug delivery device with an appropriate compatible interface. However, it may be preferable to design the module in such a way as to limit its use to one exclusive primary drug delivery device through employment of dedicated or coded features. In some situations it may be beneficial from a therapeutic and safety point of view to ensure that the medicated module is exclusive to one drug delivery device (or family of devices) while also permitting the attachment of a standard drug dispense interface to the device. This would allow the user to deliver a combined therapy when the module is attached, but would also allow delivery of the primary compound independently through a standard drug dispense interface in situations, such as, but not limited to, dose splitting (i.e. delivering the complete dose of the primary therapy in two separate injections) or top-up of the primary compound in a way that would prevent the potential risk of double dosing of the secondary compound.

A particular benefit of the disclosed medicated module may be that it makes it possible to tailor dose regimes when required, especially where a titration period is necessary for a particular drug. The medicated module could be supplied in a number of titration levels with obvious differentiation features such as, but not limited to, aesthetic design of features or graphics, numbering etc, so that a user could be instructed to use the supplied medicated module in a specific order to facilitate titration. Alternatively, the prescribing physician may provide the patient with a number of "level one" titration medicated modules and then when these were finished, the physician could then prescribe the next level. A key advantage of this titration program is that the primary device remains constant throughout.

In a preferred embodiment of our invention, the primary drug delivery device is used more than once and therefore is multi-use. Such a device may or may not have a replaceable reservoir of the primary drug compound, but our invention is equally applicable to both scenarios. In particular, a non-replaceable primary reservoir may be fixed in a reservoir holder. It is possible to have a suite of different medicated modules for various conditions that could be prescribed as one-off extra medication to patients already using a standard drug delivery device. Should the user attempt to reuse a previously used medicated module, our invention could include features that could alert the user to this situation. Such means of alerting the user may include some (or all) of the following:
1. Physical prevention of medicated module re-attachment to the primary drug deliver device once the module has been used and removed.
2. Physical prevention of re-use of the used drug dispense interface by the user (e.g. a single use needle-guard type arrangement).
3. Physical/hydraulic prevention of subsequent liquid flow through the drug dispense interface once it has been used.

4. Physical locking of the dose setter and/or dose button of the primary drug delivery device.
5. Visual warnings (e.g. change in color and/or warning text/indicia within an indication window on the module once insertion and/or fluid flow has occurred).
6. Tactile feedback (presence or absence of tactile features on the outer surface of the module hub following use).

A further feature of this embodiment may be that both medicaments are delivered via one injection needle and in one injection step. This offers a convenient benefit to the user in terms of reduced user steps compared to administering two separate injections. This convenience benefit may also result in improved compliance with the prescribed therapy, particularly for users who find injections unpleasant, or who have dexterity or computational difficulties. The use of one injection instead of two reduces the possibility for user errors and so may increase patient safety.

Our invention also covers a method of delivering two medicaments stored in separate primary packages. The medicaments may both be liquid, or alternatively one or more of the medicaments may be a powder, suspension or slurry. In one embodiment the medicated module could be filled with a powdered medicament that is either dissolved or entrained in the primary medicament as it is injected through the medicated module.

As mentioned, in the broadest scope these medicaments could be delivered via a number of routes of administration, for example needle based injections (as described), needle-free injection, inhalation etc. For example, an inhaler version of our invention could have the medicated module containing a liquid, solid or gas form of the secondary medicament that connects to an MDI or DPI inhaler. The mouthpiece would be part of the medicated module. The user would inhale through the module, actuating the MDI or DPI inhaler as normal. As the air and medicament passes through the module the second medicament, contained in the module, would become entrained in the airflow and delivered to the patient.

These as well as other advantages of various aspects of the present invention will become apparent to those of ordinary skill in the art by reading the following detailed description, with appropriate reference to the accompanying drawings.

The scope of the invention is defined by the content of the claims. The invention is not limited to specific embodiments but comprises any combination of elements of different embodiments. Moreover, the invention comprises any combination of claims and any combination of features disclosed by the claims.

BRIEF DESCRIPTION OF THE DRAWINGS

Exemplary embodiments are described herein with reference to the drawings, in which.

DETAILED DESCRIPTION

Figure 1:
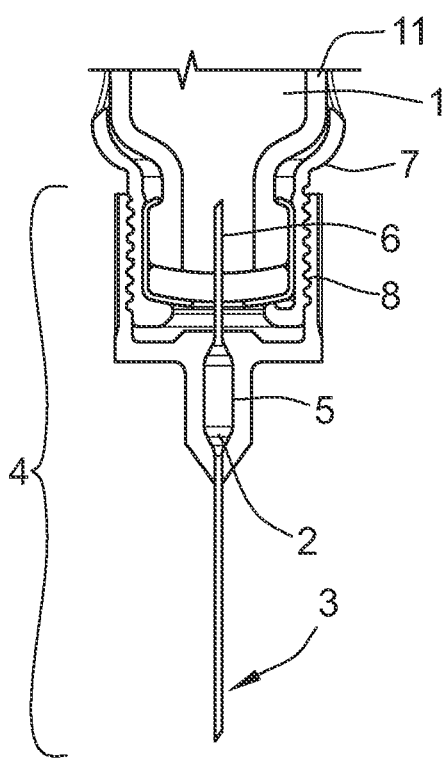
FIG. 1 illustrates an embodiment of the medicated module of the present invention having an enlarged needle portion attached to a drug delivery device.
Figure 2:
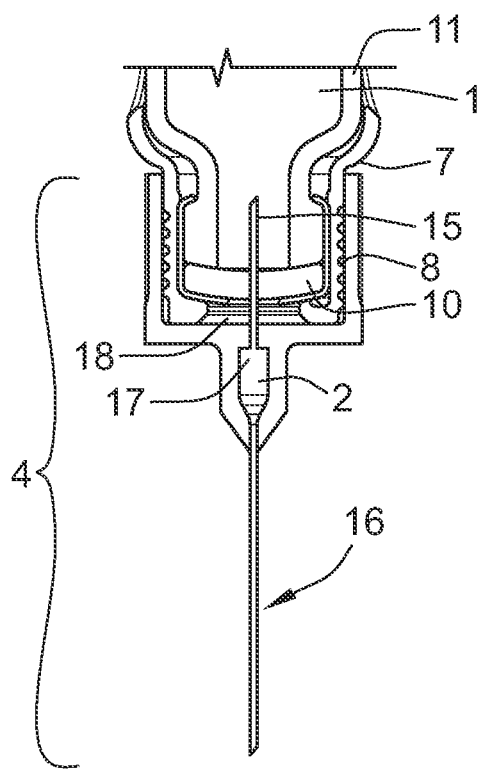
FIG. 2 illustrates an embodiment of the medicated module of the present invention having two needles connected to a secondary reservoir attached to a drug delivery device.
Figure 3:
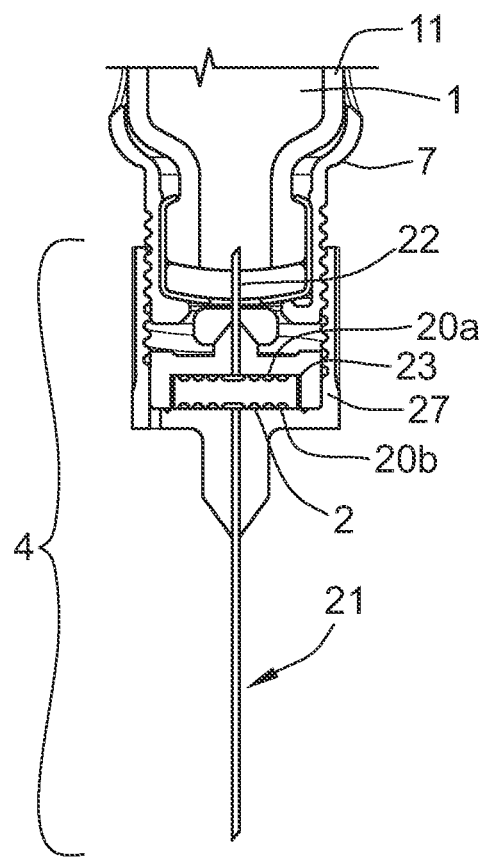
FIG. 3 illustrates an embodiment of the medicated module of the present invention having one or more spiral manifolds as part of the secondary reservoir attached to a drug delivery device.

The disclosed drug delivery system enables administering a non-user settable or fixed or predetermined dose of a second medicament (secondary drug compound) from a secondary reservoir and a variable dose of a first medicament (primary drug compound) from a primary reservoir through a single output or drug dispense interface. Setting the dose of the primary medicament by the user may automatically determine the fixed dose of the second medicament. In a preferred embodiment the drug dispense interface is a needle cannula (hollow needle). FIGS. 1-3 illustrate three different embodiments of our invention, each having a medicated module 4 attached to a drug delivery device 7. Each module is preferably self-contained and provided as a sealed and sterile disposable module that has an attachment means 8 compatible to the attachment means 9 at the distal end of device 7. Although not shown, the medicated module could be supplied by a manufacturer contained in a protective and sterile container where the user would peel or rip open a seal or the container itself to gain access to the sterile medicated module. In some instances it might be desirable to provide two or more seals for each end of the medicated module. The seal may allow display of information required by regulatory labeling requirements.

Figure 8:
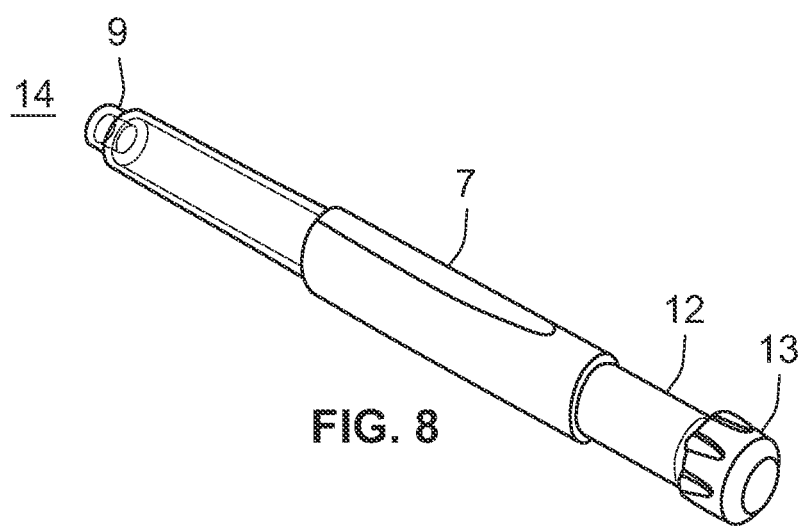
FIG. 8 illustrates one possible drug delivery device that can be used with the present invention.

One example of a drug delivery device 7 is illustrated in FIG. 8. Any known attachment means can be used, including permanent and removable connection means. Threads, snap locks, snap fits, luer locks, bayonet, snap rings, keyed slots, and combinations of such connections can be used to attach module 4 to device 7. FIGS. 1-3 illustrate the attachment means 8 as screw threads. The embodiments shown in FIGS. 1-3 have the benefit of the second medicament 2 as a single dose being contained entirely within the cannula 3 hence minimizing the risk of material incompatibility between the second medicament and the materials used in the construction of the medicated module 4.

As shown in FIG. 1 a unique aspect of this embodiment is the method of construction of output needle 3, part of which has an enlarged cross-section 5 to accommodate the volume of the fixed (single) non-user settable dose of the second medicament 2. Preferably a hydroforming or a swaging process will be utilized to form the enlarged cross-section 5 of the needle 3. Both tips of the needle are preferably not enlarged which is beneficial because it helps minimize both the physical and mental/emotional trauma associated with insertion of larger bore needles as well as minimizing the risk of compromising the sealing integrity of the septa of the primary medicament container (multiple piercing of this type of material with a relatively large gauge needle increases the risk of "coring" of the septum).

To minimize the residual volume of the second medicament that might remain in the needle module or sub-assembly 4 at the end of the dispense operation caused by recirculation, the enlarged section 5 should be designed with fluid flow characterizing models. Preferably, the design of medicated module 4 should ensure that at least about 80% of the second medicament is expelled through the distal end of needle 3, most preferably at least about 90% should be expelled. Ideally, displacement of the first medicament 1 into the proximal end 6 of needle 3 will displace the second medicament 2 without substantial mixing of the two medicaments. Preferably this is accomplished by minimizing the diametric increase and careful design of the transition from the small cross sections of the needle 3 to the enlarged cross section 5. One alternative is to have the assembly/filling process set up so as to ensure that a "plug" of gas (e.g. air or an inert gas such as nitrogen) is present in the section 6 of the needle (above the enlarged section 5) this may act to ensure that the first and second medicaments are kept separate from each other thereby help ensure sequential delivery by action of a virtual piston created by the plug of air. This plug may additionally help ensure that there is no opportunity for the primary and secondary medicaments to mix prior to injection (i.e. if the medicated module is left in the attached position for an extended period of time prior to the injection action being undertaken.

Attachment of the medicated module 4 to the multi-use drug delivery device 7 causes the engagement needle 6 located in the module to penetrate the septum 10 of cartridge 11 of the multi-use device 7. Once the engagement needle has passed through the septum of the cartridge, fluid connection is made between the first medicament 1 and the output needle 3. The dose of the multi-use device 7 is then set using a dose setter 12 (see FIG. 8) in the normal manner (e.g. by dialing out the appropriate number of units). Dispense of the medicaments is then achieved by subcutaneously injecting the medicaments via activation of a dose button 13 on device 7. The dose button of our invention can be any triggering mechanism that causes the dose of the first medicament, which was set by the dose setter, to move distally towards the distal end 14 of the device. In a preferred embodiment the dose button is operably connected to a spindle that engages a piston in the primary reservoir of the first medicament. In a further embodiment the spindle is a rotatable piston rod, e.g. a piston rod comprising two distinct threads.

Another embodiment of our invention is shown in FIG. 2 where a primary needle 15 pierces the septum 10 of the device cartridge 11 and a second needle 16 is used to subcutaneously inject the medicament. Located between the two needles is a recess 17 containing the secondary reservoir which contains the second medicament 2. The primary needle 15 is attached to a retention cap 18, which when inserted into the top of the recess 17 provides a fluid seal.

Figure 4:
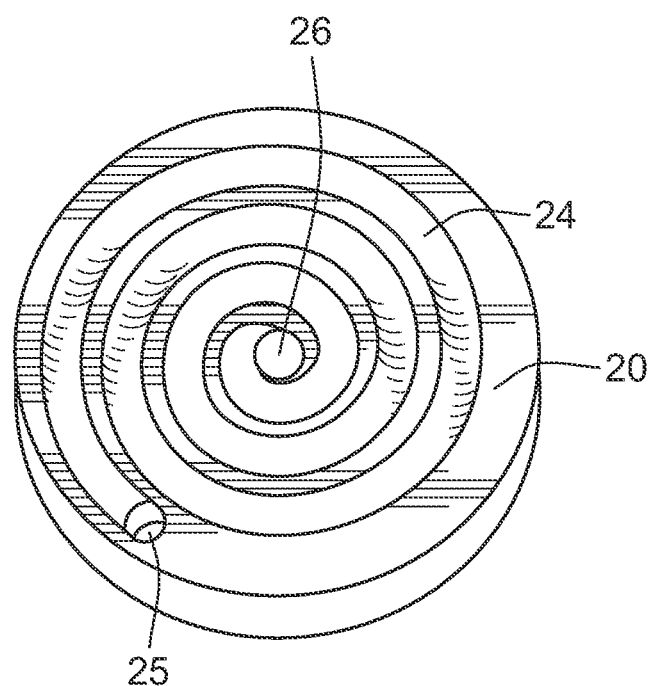
FIG. 4 illustrates a perspective view of an embodiment of one the spiral manifolds that make up part of the secondary reservoir attached to a drug delivery device.

In another embodiment (see FIG. 3) of our invention the secondary reservoir could have a fluid flow path with approximately constant cross-sectional area where the axial length is less than path length due to changing direction of path in at least one plane. One way to accomplish this configuration is through the use of one or more spiral manifolds 20 (see FIG. 4) that are used as part of the secondary reservoir to store the second medicament and to minimize the risk of mixing occurring between the two medicaments during dispense. In minimizing the risk of mixing it is desirable to minimize the cross-sectional area perpendicular to the flow direction where the two medicaments come into contact with each other. While desirable to minimize the cross-sectional area of the flow channel, the effect of this in a standard needle arrangement would be to increase the length of the flow channel for a fixed volume of the second medicament. This can result in an excessive and unacceptable axial length of the medicated module. Using one or more spiral manifolds provides a fluid path of minimal cross-sectional area, and sufficient length to store the second medicament, within an acceptable minimum axial package space.

Turning to FIG. 3, two spiral manifolds 20a & 20b (see FIG. 4 for an example of a spiral manifold) are utilized between the cartridge 11 of the reusable drug delivery device 7 and the output needle 21 to further reduce the axial package space of medicated module 4. The primary needle 22 attaches to a retention cap 23, which introduces the first medicament 1 to the center 26 of the first spiral manifold 20a. As the first medicament 1 is dispensed into spiral manifold 20a, the second medicament 2 flows radially outward along the path of the spiral groove 24 until it reaches a predetermined radial position 25 whereby the flow path traverses through the first spiral manifold. Having passed through the spiral manifold the fluid path follows a second spiral orientated such that the fluid flows radially inward on the second spiral manifold 20b. As the fluid reaches the center of the second spiral manifold 20b fluid communication is made with the output needle 21 and the medicament is dispensed through the outlet needle to the patient.

In this embodiment it is anticipated that the spiral manifolds will have sealing features along the external edges of helical groove (not shown) and/or be made from a compliant material such as rubber, TPE, or like materials, and that the assembly of the retention cap 23 into the body 27 of the medicated module will exploit these features to create a sealing labyrinth, thereby forming the helical flow channel.

Figure 5:
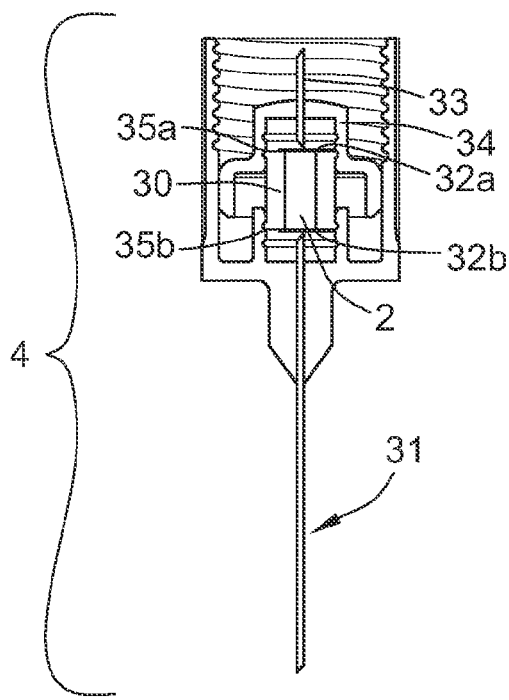
FIG. 5 illustrates an embodiment of the medicated module of the present invention having a self contained reservoir of secondary medicament having two pierceable membranes.
Figure 6:
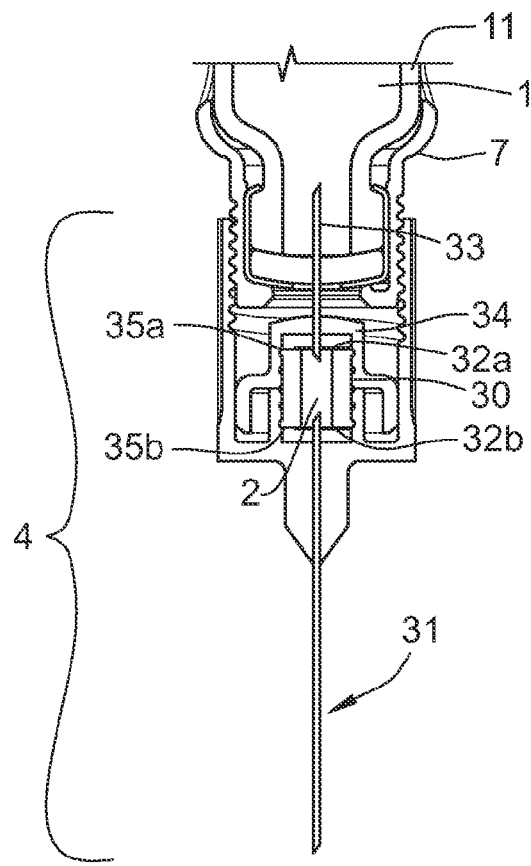
FIG. 6 illustrates an embodiment of the medicated module of the present invention having a self contained reservoir of secondary medicament having two pierceable membranes attached to a delivery device.
Figure 7:
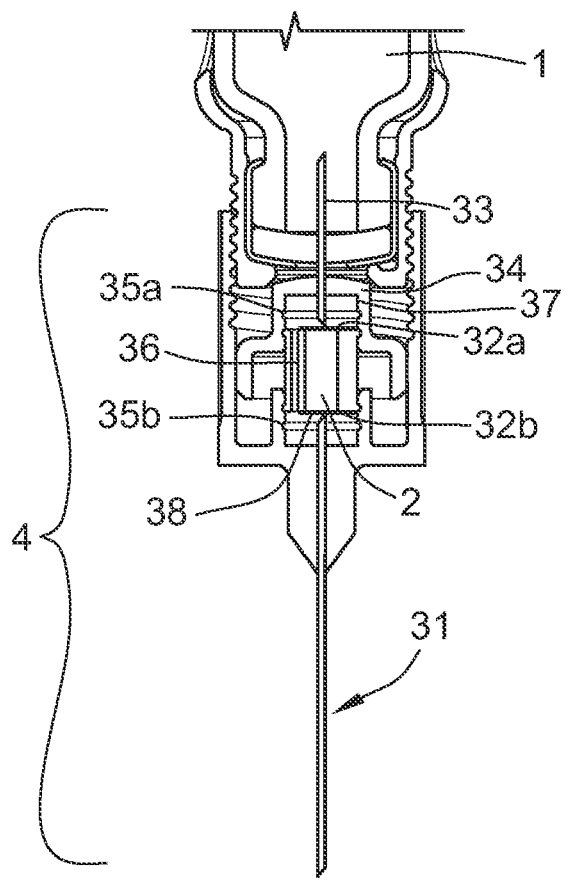
FIG. 7 illustrates an embodiment of the medicated module of the present invention having a self contained reservoir of secondary medicament having two pierceable membranes and a bypass channel.

Additional embodiments of our invention are illustrated in FIGS. 5, 6 & 7. In these embodiments the medicated module 4 contains a discrete secondary reservoir 30 containing a fixed single dose of the second medicament 2. As with the above embodiments these medicated modules administer a fixed predetermined dose of a second medicament and a variable dose of a primary medicament through a single output needle 31. As discussed in more detail below, FIG. 7 shows an alternative design of these embodiments that provides a by-pass feature preferably used for priming using the primary medicament 1.

In the embodiments shown in FIGS. 5-7 secondary reservoir 30 has ends that are sealed with pierceable membranes 32a and 32b that provide a hermetically sealed reservoir for the second medicament. A primary needle 33 can be displaced axially relative to the reservoir 30 such that in a depressed position the primary needle 33 will puncture the top membrane 32a. The output needle 31 protrudes above the lower surface of reservoir 30 and pierces the lower membrane 32b when the reservoir is moved axially relative to needle 31.

During use, on attachment of the medicated module to a multi-use drug delivery device, such as the one shown in FIG. 8, the primary needle 33 pierces septum 10 of cartridge 11 contained in device 7. This attachment causes the retention cap 34 to move distally a predetermined axial displacement so that the retention cap 34 bears against the cartridge causing the retention features 35a and 35b to be overcome and the primary needle to pierce the top membrane 32a of reservoir 30. Once the top of the reservoir bears against the retention cap, the retention features holding the reservoir in the medicated module 4 are overcome and the reservoir moves axially downward. Axial movement of reservoir 30 causes the proximal end of output needle 31 to pierce lower membrane 32*b* of reservoir 30.

In any of the above described embodiments of our invention the second medicament may be either in a powdered or other solid state, any fluid state contained within the secondary reservoir, capsule or microcapsule, or coated to the inside surface of the drug dispense interface. The greater concentration of the solid form of the medicament has the benefit of occupying a smaller volume than the liquid having lower concentration. This in turn reduces the ullage of the medicated module. An additional benefit is that the solid form of the second medicament is potentially more straightforward to seal in the secondary reservoir than a liquid form of the medicament. The device would be used in the same manner as the preferred embodiment with the second medicament being dissolved by the first medicament during dispense.

Yet another embodiment of our invention is shown in FIG. 7 where a bypass channel 36 is incorporated into the medicated module to preferably facilitate priming of output needle 31 with the first medicament 1, and/or priming of the mechanism within the device 7. During attachment of the medicated module 4 of this embodiment to a device, such as the one shown in FIG. 8, the primary needle 33 starts to pierce septum 32*a* of reservoir 30. However, prior to the primary needle completely piercing the membrane, the user has the option of initiating a priming operation utilizing bypass channel 36. This is achieved by dispensing the primary medicament into the cavity 37 between the retention cap 34 and the top pierceable membrane 32*a*. Since the cavity 37 is in fluid communication with bypass channel 36, the primary medicament flows around reservoir 30 and into lower cavity 38 and out through output needle 31. After the optional priming operation is complete, the medicated module can be fully attached (rotated in the case of screw threads) to the multi-use device 7 causing the output and primary needles to pierce the lower and top membranes of the reservoir, respectively. Piercing of membranes 32*a* and 32*b* opens fluid communication between the first and second medicaments allowing them to be dispensed through operation of the dispense mechanism on the multi-use device. When this occurs bypass channel 36, and cavities 37 and 38 are isolated from the contents of reservoir 30. To allow the assembly to move axially downward fully into the "ready to use" state (as illustrated in FIG. 6) features may be present in the invention to ensure that any primary medicament in cavities 37 or 38 during this final attachment operation is either expelled into the output needle, or safely contained in a separate region of the medicated module that is not in fluid communication with the outlet needle during use. Differentiation between the priming and fully attached states of the medicated module relative to the multi-use device could be achieved by though indicators such as tactile, audible, visual and the like design features.

The connection or attachment between the medicated module according to the invention may contain additional features (not shown), such as connectors, stops, splines, ribs, grooves, pips, clips and the like design features, that ensure that specific medicated modules are attachable only to matching drug delivery devices. Such additional features would prevent the insertion of a non-appropriate medicated module to a non-matching injection device.

The shape of the medicated module may be a cylindrical body or any other geometric shape suitable for defining a fluid reservoir or for containing discrete self-contained reservoir of the secondary medicament and for attaching one or more needle cannula. The secondary reservoir can be manufactured from glass or other drug contact suitable material. The integrated injection needle can be any needle cannula suitable for subcutaneous or intramuscular injection.

Additionally, the medicated module according to the invention could incorporate a safety shield device that would prevent accidental needle sticks and reduce the anxiety experienced by users who suffer from needle phobia. The exact design of the safety shield is not critical to our invention, however, a preferred design is one that is operably connected to the first and/or second reservoirs. In such a design the activation of the safety shield could unlock the drug delivery system or instigate fluid communication between the reservoirs and in some cases cause the second medicament to be dispensed prior to activating the dose button to dispense the primary medicament from the first reservoir. Another preferred design would physically prevent insertion of the used drug dispense interface into the patient (e.g. a single use needle-guard type arrangement).

Preferably the medicated module is provided by a manufacturer as a stand-alone and separate device that is sealed to preserve sterility. The sterile seal of the module is preferably designed to be opened automatically, e.g. by cutting, tearing or peeling, when the medicated module is advanced or attached to the drug delivery device by the user. This opening of the seal may be assisted by features such as angled surfaces on the end of the injection device or features inside the module. The seal may also be provided by an over wrap or manual tear off, removable element.

The medicated module of our invention may be designed to operate in conjunction with a multiple use injection device, preferably a pen-type multi-dose injection device, similar to what is illustrated in FIG. 8. The injection device could be a reusable or disposable device. By disposable device it is meant an injection device that is obtained from the manufacturer preloaded with medicament and cannot be reloaded with new medicament after the initial medicament is exhausted. The device may be a fixed dose or a settable dose. Likewise, it can be a single dose device or a multi-dose device.

A typical injection device contains a cartridge or other reservoir of medication, i.e. the primary or master reservoir containing the first medicament 1. This cartridge is typically cylindrical in shape and is usually manufactured in glass. The cartridge is sealed at one end with a rubber bung and at the other end by a rubber septum. The injection pen is designed to deliver multiple injections from the primary reservoir. The delivery mechanism is typically powered by a manual action of the user, however, the injection mechanism may also be powered by other means such as a spring, compressed gas or electrical energy.

In certain embodiments where the medicated module contains a single dose of a medicament, the module may have to be attached to a drug delivery device in order to administer the single dose in the reservoir to a patient. In other words, the medicated module may not be configured to be used as a stand-alone injection device. This is because the module does not have a dose delivery mechanism and instead relies on the dose delivery mechanism contained in the drug delivery device to which it must be attached.

Exemplary embodiments of the present invention have been described. Those skilled in the art will understand, however, that changes and modifications may be made to these embodiments without departing from the true scope and spirit of the present invention, which is defined by the claims.

LIST OF REFERENCES 1 first medicament
2 second medicament
3 cannula/needle/output needle
4 module/sub-assembly
5 enlarged (cross-)section
6 section of needle/engagement needle
7 drug delivery device
8 attachment means
9 attachment means at distal end of drug delivery device
10 septum
11 cartridge
12 dose setter
13 dose button
14 distal end of device
15 primary needle
16 second needle
17 recess
18 retention cap
20, 20a, 20b spiral manifolds
21 output needle
22 primary needle
23 retention cap
24 path of the spiral groove
25 radial position
26 center of spiral manifold
27 body of medicated module
30 secondary reservoir
31 output needle
32a, 32b pierceable membranes/septums
33 primary needle
34 retention cap
35a, 35b retention features
36 bypass channel
37 cavity
38 lower cavity

We claim:

1. A drug delivery system operable to deliver a first medicament and a second medicament through a single dispense interface, comprising:
   a primary drug delivery device comprising:
      a primary reservoir containing the first medicament, wherein the first medicament comprises at least one first drug agent, and wherein the primary reservoir comprises a pierceable seal, and
      a dose button operably connected to the primary reservoir; and
   a medicated module configured to be attached to a distal end of the primary drug delivery device, the medicated module comprising:
      an engagement interface configured such that attachment of the medicated module to the distal end of the primary drug delivery device causes the engagement interface to pierce the pierceable seal of the primary reservoir,
      a dispense interface configured for fluid communication with the primary reservoir via the engagement interface, and
      a secondary reservoir containing the second medicament, wherein the second medicament comprises at least one second drug agent, and wherein the secondary reservoir is configured for fluid communication with the dispense interface,
   wherein the medicated module is configured such that when the medicated module is attached to the distal end of the primary drug delivery device, a single activation of the dose button causes the first medicament from the primary reservoir and a non-user settable dose of the second medicament to be expelled through the dispense interface, and
   where the single activation of the dose button causes the first medicament from the primary reservoir to be expelled through the dispense interface after a therapeutic dose of the non-user settable dose of second medicament has been expelled through the dispense interface.

2. The system of claim 1 comprising a housing containing a single dose setter operably connected to the primary reservoir of the first medicament.

3. The system of claim 1, where at least one of the secondary reservoir and the primary reservoir contains a single dose.

4. The system of claim 1 where at least one of the primary reservoir and the secondary reservoir contains a liquid medicament.

5. The system of claim 1 where at least one of the primary reservoir and the secondary reservoir contains multiple doses of medicament.

6. The system of claim 1 where the dispense interface is a hollow needle.

7. The system of claim 1 where the medicated module is disposable and replaceable with a replacement module containing a new secondary reservoir of medicament and a new dispense interface.

8. The system of claim 7 where the medicated module contains a safety shield.

9. The system of claim 1 where at least one of the primary reservoir and the secondary reservoir is replaceable.

10. The system of claim 1 where at least one of the primary reservoir and the secondary reservoir is in fluid communication with the dispense interface.

11. A method of dispensing a first medicament and a second medicament from separate reservoirs, comprising, in combination, the steps of:
   providing a primary drug delivery device comprising:
      a primary reservoir containing the first medicament, wherein the first medicament comprises at least one first drug agent, and
      a dose button operably connected to the primary reservoir;
   providing a medicated module configured to be attached to a distal end of the primary drug delivery device, the medicated module comprising:
      a dispense interface configured for fluid communication with the primary reservoir, and
      a secondary reservoir containing the second medicament, wherein the second medicament comprises at least one second drug agent, and wherein the secondary reservoir is configured for fluid communication with the dispense interface;
   attaching the medicated module to the distal end of the primary drug delivery device;
   activating the dose button, wherein activation of the dose button causes the first medicament from the primary reservoir and a non-user settable dose of the second medicament from the secondary reservoir to be expelled through the dispense interface, and
   where the activation of the dose button causes the first medicament from the primary reservoir to be expelled through the dispense interface after a therapeutic dose of the non-user settable dose of second medicament has been expelled through the dispense interface.

12. A method of dispensing a non-user settable dose of a second medicament and a dose of a first medicament from separate reservoirs, comprising, in combination, the steps of:
 a) setting a dose of the first medicament contained in a primary reservoir using a single dose setter of a primary drug delivery device, the primary reservoir comprising a pierceable seal;
 b) attaching a medicated module to a distal end of the primary drug delivery device,
 wherein attachment causes a dispense interface to pierce the pierceable seal of the primary reservoir, and
 wherein the medicated module comprises a secondary reservoir containing the second medicament;
 c) moving the set dose of the first medicament from the primary reservoir causing it to flow in a distal direction; and
 d) expelling the set dose of the first medicament through the dispense interface of the medicated module after expulsion of a therapeutic dose of a non-user settable dose of the second medicament through the dispense interface of the medicated module.

13. The method of claim 12, wherein expelling the set dose of the first medicament from the primary reservoir simultaneously forces the non-user settable dose of the second medicament through the dispense interface.

14. The method of claim 12, wherein at least 80% of the second medicament is expelled through the dispense interface.

15. The system of claim 1, wherein the engagement interface comprises a needle.

* * * * *